United States Patent [19]

Gallacher et al.

[11] Patent Number: 5,266,720
[45] Date of Patent: Nov. 30, 1993

[54] DERIVATIVES OF HYDROXYMETHOXY MANDELIC ACID (HMMA), HOMOVANILLIC ACID (HVA), ANTIBODIES AND LABELLED SUBSTANCES PREPARED THEREFROM, AND IMMUNOASSAYS USING THESE

[75] Inventors: Gerard Gallacher, London; Geoffrey W. Mellor, Hayes; Yee-Ping Ho, New Malden, all of England

[73] Assignee: Cancer Research Campaign Technology Limited, London, England

[21] Appl. No.: 721,526

[22] PCT Filed: Jan. 12, 1990

[86] PCT No.: PCT/GB90/00048
§ 371 Date: Jul. 8, 1991
§ 102(e) Date: Jul. 8, 1991

[87] PCT Pub. No.: WO90/08133
PCT Pub. Date: Jul. 26, 1990

[30] Foreign Application Priority Data

Jan. 12, 1989 [GB] United Kingdom ............... 8900666

[51] Int. Cl.$^5$ .............................................. C07C 69/76
[52] U.S. Cl. ......................................... 560/60; 560/55; 560/53; 560/42; 530/405; 530/309.8; 549/223; 435/793
[58] Field of Search ................. 560/60, 55, 53, 42

[56] References Cited

U.S. PATENT DOCUMENTS 4,041,076  8/1977  Avenia et al. ..................... 260/559

OTHER PUBLICATIONS

J. Immunological Methods vol. 118, No. 1 (Mar. 1989) Mellor et al "Production and characterization of antibodies . . . " pp. 101-107.
J. Clin Chem. Clin. Biochem., vol. 22, No. 11, (1984) Knoll et al "Problems in the development of radioimmunoassay . . . " pp. 741-749.
Int. J. Peptide Protein Res.s, vol. 30, No. 2, (1987) Albericio et al "An acid-labile anchoring linkage for solid--phase synthesis . . . " pp. 206-216.
Chemical Abstracts, vol. 76, No. 15, (Apr. 1972) Liebman et al "Synthesis of homovanillic acid-2-. . . " p. 394, Abstract 85528v.

*Primary Examiner*—Paul J. Killos
*Attorney, Agent, or Firm*—Nixon & Vanderhye

[57] ABSTRACT

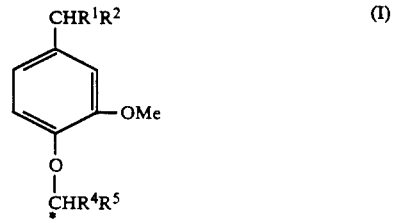

Compounds of formula (I), wherein $R^1$ is hydrogen or hydroxyl. $R^2$ is a reversibly protected carboxyl group, $R^4$ is H or $C_1$-$C_3$ alkyl and $R^5$ is a substituent having a pi electron system alpha to the asterisked carbon atom, and containing one or more of a carboxyl, an amine, or an aldehyde group, are prepared by reversibly protecting the carboxyl group of hydroxymethoxy mandelic acid or homovanillic acid and reacting the phenolic hydrogen with an alkylating agent such as methylbromoacetate, to introduce an ester group, followed by selective hydrolysis. The compound of formula (I) can be coupled, for example by means of an active ester, to either a carrier protein for the preparation of an immunogen, or to a label, such as a fluorescent label, a radioisotope, or an enzyme.

4 Claims, No Drawings

DERIVATIVES OF HYDROXYMETHOXY MANDELIC ACID (HMMA), HOMOVANILLIC ACID (HVA), ANTIBODIES AND LABELLED SUBSTANCES PREPARED THEREFROM, AND IMMUNOASSAYS USING THESE

This invention relates to the production of derivatives of hydroxymethoxy mandelic acid (HMMA) and homvanillic acid (HVA), to their use in raising antibodies, and in the production of labelled compounds, and to the use of such materials in immunoassays for HMMA and HVA.

HMMA and HVA are compounds of the formula

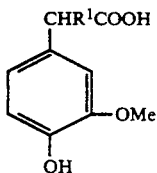     II in which $R^1$ and $R^3$ have the following definitions:

| $R^1$ | Compound Name |
|---|---|
| OH | Hydroxymethoxy Mandelic Acid (HMMA) |
| H | Homovanillic acid (HVA) |

They are major urinary metabolites of andrenaline, noradrenaline or dopamine (catecholamines which play an essential role in the regulation of the neuroendocrine system (Axelrod & Weinshilboum, (1972), New Engl. J. Med 287, 237)).

The output of these metabolites is markedly raised in neural crest tumours such as phaeochromocytoma and neuroblastoma (Robinson, "Tumours that secrete catecholamines" John Wiley & Sons (1980)). Screening for these tumours would be facilitated by simple, reliable and inexpensive assays for HMMA and HVA, but as yet none is available.

Presently the most widely used technique for assay of HMMA is the Pisano spectrophotometric assay (Pisano et al Clin. Chem Act (1962), 7, 285, which is subject to both drug and dietary interferences (Rock, Diagn. Med. (May 1985), 21). There are also high pressure liquid chromatography and gas liquid chromatography assays for HMMA (Krstulovic, "Quantitantive Analysis of Catecholamines and related compounds" John Wiley & Sons, (1986)), but these are expensive, technically demanding, and have a limited sample throughput.

Immunoassays are ideal for screening large sample numbers but at present there are no good methods for the raising of antibodies and the development of immunoassays to HMMA and HVA. Some limited success has been achieved when a Mannich reaction is used to couple the hapten to a carrier protein (e.g. Yoshioaka et al, Biogenic Amines (1987), 4, 211-17, 219-27 and 229-35, and Kazak et al, Lab Delo 1983, (5), 20-2) but this approach lacks chemical control and reproducibility (see, for example, "Problems in the Development of Radioimmunoassay of Catecholamines" by E. Knoll & H. Wisser (J. Clin Chem. Clin. Biochem Vol. 22 (1984) 741-749)).

In accordance with the present invention, a derivative of the above compounds of formula II is prepared by protecting the carboxyl group preferably with a sterically hindered protecting group such as benzhydryl henhydryl or t-butyl and subsequently reacting the phenolic hydroxyl with an alkylating agent such as methyl bromoacetate to introduce an ester group. Selective hydrolysis of the introduced ester group gives a protected derivative, which can be coupled, for example by means of an active ester, to either a carrier protein for the preparation of an immunogen, or to a label, such as a fluorescent label, a radioisotope, or an enzyme.

The deprotection of the carboxyl group preferably with a base yields the immunogen or the labelled happen respectively.

The protection of functional groups in the preparation of chemical compounds is well known, for example EP 0278911 (Ciba-geigy) discloses a method of protecting amine groups in the preparation of bicyclic beta lactam carboxylic acids. Albericio et al (int. J. Peptide Protein Res., Vol. 30, No. 2, 1987, pages 206–216) discloses a method for the selective protection of amine groups, in the preparation of polymer-supported phenylmethylamines. U.S. Pat. No. 4,041,076 (Avenia) is concerned with assays for detection of phenethylamine compounds, and discloses the selective protection of amine groups in amphetamine-type compounds.

In a first aspect of the invention, there is provided a compound of the formula

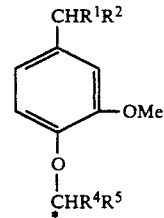     I wherein $R^1$ is hydrogen or hydroxyl, $R^2$ is a reversibly protected carboxyl group, $R^4$ is H or $C_1$–$C_3$ alkyl and $R^5$ is a substituent having a pi electron system alpha to the linking (asterisked) carbon atom, and containing one or more of a carboxyl, an amine, or an aldehyde group.

The protection of the carboxyl group is preferably carried out by converting it to a sterically hindered ester, for example a group of the formula

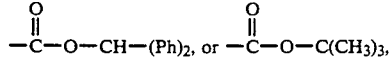

The protecting group should be neutral, not easily alkylated, and should be easily removed, usually by hydrolysis, when desired.

The preferred protecting group is benzhydryl.

The protection of the compounds of formula II may be carried out by treatment with a solution of diphenyldiazomethane (as described by Kumar and Murray, J. Amer Chem. Soc. (1984), 106, 1040) in dichlormethane, to produce the benzhydryl group.

The linking reaction of the protected compound of Formula II is preferably carried out utilising an alkylating agent which is capable of carrying out an alkylation reaction at a temperature of less than 50° C. The alkylating agent contains a suitable leaving group (preferably a halogen, more preferably bromine or iodine, or a tosylate, mesylate, or triflate group) which is located alpha to a pi electron system which functions as an activating group. Suitable activating pi-containing groups are a carbonyl group, an aromatic residue, or an alkenyl double bond. Preferred alkylating agents are methyl bromoacetate, methyl bromocraotonate, and methyl bromomethyl benzoate.

The protected derivatives of formula I may be linked to a carrier protein and the protecting group removed, by methods which are per se conventional, to produce an antigenic substance containing a structure of the formula

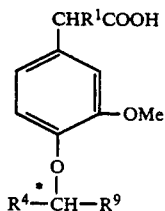

III

This antigenic substance may be employed for raising antibodies to compounds of the formula II.

The protected derivatives of formula I may also be linked with a detectable label, for example an enzyme, a fluorescent substance, or a substance incorporating a radioactive isotope and subsequently deprotected, again by per se conventional means, to produce a labelled derivative of a compound of formula II, which contains a structure of formula III as defined above, linked to a detectable label.

Linking of the derivative of formula I with the carrier protein or label may be carried out utilising a suitable coupling agent. Subsequently the group $R^2$ may be deprotected, for example by acid or base hydrolysis, to yield the corresponding compound of formula II, linked to the carrier protein or label. The hydrolysis is preferably carried out in basic conditions. The coupling agent is preferably a carbodiimide, such as 1-ethyl-3(3-dimethylaminopropyl)-carbodiimide-hydrochloride. Coupling may also be achieved by means of an activated ester, for example an N-hydroxy succinimide activated ester.

The antigenic substance prepared in accordance with the invention may be used for the generation of antibodies to compounds of the formula II above, by innoculation into an animal, using generally known techniques. The resulting antibodies may be polyclonal antibodies, or monoclonal antibodies, prepared in accordance with the methods of Kohler and Millstein.

The resulting polyclonal or monoclonal antibodies may be utilised in standard immunoassay techniques, for example using enzyme, radioisotopic, or fluorescent labels.

Such assays are preferably so-called "competition" assays, in which a limited amount of antibody (which may either be an antibody prepared in accordance with the invention, or a different antibody to the metabolite in question) is provided, and labelled and unlabelled hapten compete for binding sites.

A number of preferred embodiments of the invention are described in the following examples.

EXAMPLE I

Production of Protected HMMA Derivative of Formula I (a) Benzhydryl protection of HMMA HMMA (formula II, $R^1$=OH, 1. g; 5.05 mmol) in dichloromethane-methanol (4:1; 20 ml) was treated with a solution of diphenyldiazomethane in dichloromethane until the purple colour just remained. After stirring for 15 minutes at room temperature, the solvent was removed in vacuo, and the residue taken up in ethyl acetate, washed with 1M sodium bicarbonate and water, dried and concentrated in vacuo to yield a yellow solid. This was recrystallised from ethyl acetate-cyclohexane (1:1) to yield a white solid (1.05 g; 61%) of melting point 120°–122° C.

(b) Preparation of Benzhydryl-4-0-methylcarboxymethyl HMMA

Benzhydryl HMMA prepared in accordance with (a) above (1 g; 2.74 mmol) in dry dimethoxyethane (10 ml) was treated with sodium hydride (60% dispersion; 110 mg; 2.74 mmol) and stirred at room temperature for 30 minutes. Methylbromacetate (462 mg; 285 microliters; 3.02 mmol) was added, and the reaction mixture stirred overnight. Solvent was removed in vacuo and the residue purified by flash chromatography on silica (eluting solvent dichloromethane-methanol 99:1). The column fractions were concentrated, and the resultant oil crystallised from acetone-cyclohexane (3:7) to give white crystals (580 mg; 48%) of melting point 110°–111° C.

(c) Preparation of Benzhydryl-4-0-carboxymethyl HMMA

The resulting compound (580 mg; 1.33 mmol) in tetrahydrofuran (16 ml) and water (6.7 ml) was treated with 1M sodium hydroxide (1.33 ml; 1.33 mmol) and stirred at room temperature for 1 hour to selectively hydrolyse the methyl carboxymethyl ester group. Solvent was removed in vacuo and the residual partitioned between ethyl acetate and 0.1M hydrochloric acid. The organic phase was dried and concentrated to give a clear oil which was crystallised from ethyl acetate to give white crystals (249 mg; 44%) of melting point 103°–106° C., the target compound.

All steps in the synthesis proceeded in moderate to good yield, and satisfactory spectroscopic data (consisting of 250 MHz $^1$H nuclear magnetic resonance, infrared, and mass spectra) were obtained for all of the intermediates. The saponification of the methyl ester was virtually selective, with minimal hydrolysis of the benzhydryl ester.

EXAMPLE 2

Production of HMMA Immunogen

The product of Example 1 (72 mg; 0.17 mmol) in acetonitrile (2 ml) was treated with N-hydroxysuccinimide (20 mg; 0.17 mmol) and 1-ethyl-3-(3-dimethylaminopropyl)-carbodiimide hydrochloride (50 mg; 0.26 mmol) and stirred at room temperature for 45 minutes, after which time thin-layer chromatography (TLC) showed complete formation of an active ester of the protected compound of formula I (developing solvent dichloromethane-methanol 3:1; $R_f$ 0.95). The active ester solution was added dropwise over a period of 15 minutes, to a solution of keyhole-limpet haemocyanin (KLH) (100 mg; 0.33 micromoles) in a phosphate-saline buffer (pH 8, 10 ml) and pyridine (2 ml). The mixture was stirred overnight, dialysed against running tap water for three days and the residue lyophilised to yield the protected conjugate (99 mg). The hapten/carrier coupling ratio was examined by UV spectrometry at 280 nm and found to be 321 molecules of benzhydryl HMMA per molecule of KLH.

The thus-prepared conjugate (99 mg) was treated with 1M sodium hydroxide (10 ml) for 2.5 hours at room temperature. The mixture was cooled in ice and 2M hydrochloric acid (4.5 ml) added to give a pH 10 solution which was taken to pH 4 with 1M citric acid (6 ml). Dialysis as above and lyophilisation yielded the immunogen (94 mg).

EXAMPLE 3

PREPARATION OF LABELLED HMMA

Benzhydryl-4-O-carboxymethyl HMMA (10 mg; 24 micromole) in acetonitrile (1 ml) was converted to the active ester by the method described in Example 2, and a solution of fluoresceinthiocarbamylethylene (FTCED); (8 mg; 18 micromole) in water-triethylamine (1:1; 200 micromole) was added.

After stirring for 30 minutes at room temperature, the solvent was removed in vacuo and the residual treated with 1M hydrochloric acid. The resultant orange solid was filtered, dissolved in methanol, and purified by TLC (eluent dichloromethane-methanol 3:1) to give one major band $R_f$ 0.73, which was eluted with the same solvent system.

The resulting compound was deprotected, by treatment with 1M sodium hydroxide (500 microlitre) for 30 minutes at room temperature in the dark. The reaction mixture was taken to pH 3 with 2M hydrochloric acid (200 microlitre) and the 1M citric acid (1.5 ml). Volatiles were removed in vacuo, the residue taken up in methanol, and inorganics filtered to leave a clear yellow solution. This was subjected to TLC (eluent dichloromethane-methanol-acetic acid 75:25:1) to give the product as one major band $R_f$ 0.10, which was eluted with methanol and stored at $-20°$ C. in the dark.

EXAMPLE 4

Production of polyclonal sheep antibodies

Sheep were immunised using standard techniques with 4 mg of the product of Example 2, and boosted with 2 mg doses at 4 weekly intervals. Serum was collected using standard techniques.

EXAMPLE 5

Immunoassay Method

Assays were performed in pH 7.5, 50 mmolar phosphate buffer containing 0.1% sodium azide as preservative. The buffer for polarisation fluoroimmunoassay (PFIA) also contained 0.1% bovine gamma globulin to prevent antibody adherence to the glass cuvettes employed, and the buffer for separation fluoroimmunoassay (SFIA) contained 0.1% of a detergent (Trade Mark TRITON X-100) to prevent particle aggregation, and aid decanting.

The methanolic solution of labelled hapten produced in Example 3 (50 microlitre) was dissolved in 50 mmolar bicarbonate (pH 9.0, 2 ml), and the concentration determined at 492 nm, assuming the molar extinction coefficient of fluorescein to be $8.78 \times 10^4 L\ mol^{31}\ ^1cm^{-1}$ according to the method of Pourfarzaneh et al (Clin Chem (1980) 26, 730). This solution was diluted to 30 nmolar for PFIA tests, and 150 nmolar for SFIA tests, in the assay buffers described above.

PFIA Assay

Standards were prepared by dissolving HMMA (10 mg) in buffer (10 ml, to give 1 g per liter solution), and diluting this to give solutions of 0, 1, 5, 10, 50, 100, 500 and 1,000 mg per liter. Standard or sample (10 microlitre) and label (500 microlitre) were vortex-mixed, incubated with antiserum (500 microlitres of a dilution sufficient to give a reading of 200 mP in the absence of standard), and incubated for one hour. The polarisation fluorescence of each tube was read.

SFIA Assay Method

Antisera prepared as in Example 4 above were coupled to a magnetisable solid phase, using cyanogen bromide, according to the method of Sidki et al (Ann. Clin. Biochem (1983) 20, 227), to give a suspension of 1 mg of solid phase in 20 ml of buffer, which was stored at 4° C. until required.

Standards prepared as above or samples (500 microlitre) were vortex-mixed with labelled hapten (150 nmol 100 microlitre) prepared as in Example 3, and to this was added solid phase antibody (100 microlitre of a dilution sufficient to bind 50% of the label in the absence of standards). After incubation with constant shaking for 1 hour, buffer was added and the tubes were sedimented, decanted, eluted with a solution of pH9, 50 nanomolar bicarbonate buffer/methanol (1:4, 1.4 ml) and the fluorescence of the supernatant read and compared against a total tube containing label (100 microliter) and elution reagent (1.4 ml), to give percentage bound.

The cross reactivity of the antibodies was tested with structurally similar compounds, by SFIA at 50% binding, according to the method of Abraham (J. Clin. Endocrinol. Metab. (1969) 29, 866). The structurally similar compounds tested were vanillylmandelic acid, 4-hydroxylmandelic acid, 3,4-dihydroxymandelic acid, mandelic acid, homovanillic acid, vanillic acid, 4-hydroxy-3-methoxy-phenylacetic acid, 4-hydroxy-3-methoxyphenyl glycol, adrenaline, noradrenaline, dopamine, dopa, metanephrine, normetanephrine and 3-methoxytyramine. All showed low levels of binding, in comparison with HMMA.

EXAMPLE 6

Production of protected homovanillic acid derivative of Formula I (Formula I, $R^1$=H, $R^2$=NH.CH.OOCH(Ph)$_2$, $R^4$=H, $R^5$=COOH)

Example 1 was repeated, using homovanillic acid as a starting material, in place of normetanephrine hydrochloride. The resulting derivative had a melting point of 137° to 140° C.

By methods analogous to those described above, the protected homovanillic acid derivative was used in the preparation of imunogens and labelled derivatives. The imunogen was used for raising antibodies, as described in Example 4, and the antibodies were utilised in immunoassays for the target compound, as described in Example 5.

It will of course be appreciated that, instead of the fluorescent label described in Example 3, any one of the many known enzyme labels (for example horesradish peroxidase or alkaline phosphatase) or radioactive labels, (for example 125 I-histamine or $^3$H) can be utilised in the method of Example 3, with corresponding modifications to the assay method of Example 5. Furthermore, the antibody production method may be modified to produce monoclonal antibodies, in accordance with the method of Kohler and Millstein.

We claim:

1. A compound of the formula

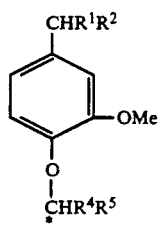

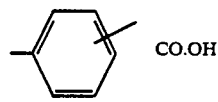

wherein $R^1$ is hydrogen or hydroxyl, $R^2$ is a reversibly protected carboxyl group, $R^4$ is H or $C_1$-$C_3$ alkyl and $R^5$ is a substituent having a pi electron system alpha to the asterisked carbon atom, and containing one or more of a carboxyl, an amine, or an aldehyde group.

2. A compound as claimed in claim 1, wherein $R^4$ is hydrogen and $R^5$ is a group of the formula —CO.$R^6$, —CH=CH—$R^7$, or wherein $R^6$ is OH, $C_1$-$C_{20}$ alkylene or $C_2$-$C_{20}$ alkenylene bearing a carboxy, amine, or aldehyde substituent, and $R^7$ is COOH, CHO, or a $C_1$-$C_{20}$ alkylene or a $C_2$-$C_{20}$ alkenylene group having a carboxy, aldehyde or amine substituent.

3. A compound as claimed in claim 2, wherein $R^5$ is COOH, or CH=CH.COOH.

4. A compound as claimed in claim 1, wherein $R^2$ is a group of the formula

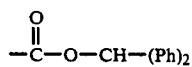

or a group of the formula

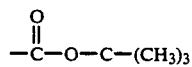

* * * * *